United States Patent [19]

Knollmueller

[11] 4,058,546
[45] Nov. 15, 1977

[54] ALKOXYSILANE DOUBLE CLUSTER COMPOUNDS WITH SILICONE BRIDGES AND THEIR PREPARATION AND USE

[75] Inventor: Karl O. Knollmueller, Hamden, Conn.

[73] Assignee: Olin Corporation, New Haven, Conn.

[21] Appl. No.: 791,671

[22] Filed: Apr. 28, 1977

[51] Int. Cl.² ............................. C07F 7/04; C07F 7/18
[52] U.S. Cl. ...................... 260/448.8 R; 260/448.8 A; 252/67; 252/78.3
[58] Field of Search ................... 260/448.8 R, 448.8 A

[56] References Cited

U.S. PATENT DOCUMENTS

| 3,308,148 | 3/1967 | Hahn et al. ............... 260/448.8 R X |
| 3,960,913 | 6/1976 | Knollmueller ............... 260/448.8 R |
| 3,965,135 | 6/1976 | Knollmueller ............... 260/448.8 A |
| 3,965,136 | 6/1976 | Knollmueller ............... 260/448.8 A |

Primary Examiner—Paul F. Shaver
Attorney, Agent, or Firm—Robert J. Feltovic; Thomas P. O'Day; F. A. Iskander

[57] ABSTRACT

Novel alkoxysilane cluster compounds are described having the formula:

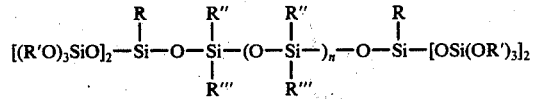

wherein $n$ is an integer from 0 to 300; R is hydrogen, alkyl, alkenyl, aryl, aralkyl or $-OSi(OR')_3$; each R' is independently selected from alkyl, alkenyl, aryl or aralkyl with the proviso that at least a majority of R' radicals are sterically hindered alkyl groups having at least 3 carbon atoms; and R" and R''' are independently selected from hydrogen, alkyl, alkenyl, aryl, aralkyl, hydroalkyl, and halo or cyano substituted alkyl, alkenyl, aryl, aralkyl, and hydroalkyl. The preparation and use of these alkoxysilane cluster compounds also are described.

18 Claims, No Drawings

ALKOXYSILANE DOUBLE CLUSTER COMPOUNDS WITH SILICONE BRIDGES AND THEIR PREPARATION AND USE

BACKGROUND OF THE INVENTION

Silicate esters, silanes, silanols, oxysilanes and oxysilanols are well known for their utility as functional fluids and many of these compounds have been proposed for use as heat transfer fluids, hydraulic fluids, brake fluids, transmission fluids and the like.

Alkoxysilanol and alkoxysilane compounds which are silicon-oxygen balanced cluster compounds are the subjects of U.S. Pat. No. 3,965,135 and U.S. Pat. No. 3,965,136, issued to the present inventor. These cluster compounds, however, are single cluster compounds in contrast to the double clusters of the present invention.

In addition, alkoxysilane compounds featuring multiple cluster units also have been illustrated by the present inventor in U.S. Pat. No. 3,992,429. These multiple cluster compounds are defined as exhibiting the general formula:

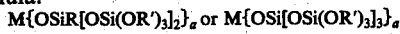

wherein $a = 2$, 3, or 4; and M is a substituted or unsubstituted branched or straight chain hydrocarbon di-, tri-, or tetraradical having up to 25 carbon atoms. As indicated, these multiple cluster compounds feature a hydrocarbon bridge M, unlike the subject silicon-bridged double clusters.

SUMMARY OF THE INVENTION

Novel alkoxysilane compounds, which have heretofore not been described in the literature, have now been developed. These alkoxysilane compounds which exhibit desirable functional fluid properties are double cluster compounds with silicone bridges having the general formula:

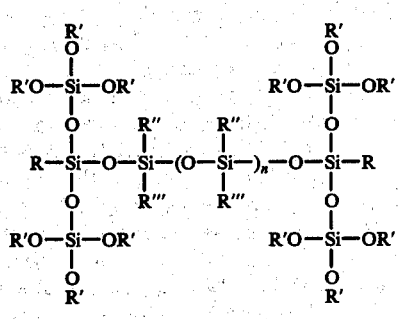

(I)

wherein $n$ is an integer from 0 to 300; R is hydrogen, alkyl, alkenyl, aryl, aralkyl or —OSi(OR')$_3$; each R' is independently selected from alkyl, alkenyl, aryl or aralkyl with the proviso that at least a majority of R' radicals are sterically hindered alkyl groups having at least 3 carbon atoms; and R'' and R''' are independently selected from hydrogen, alkyl, alkenyl, aryl, aralkyl, hydroalkyl, and halo or cyano substituted alkyl, alkenyl, aryl, aralkyl, and hydroalkyl. A method for preparation of the novel alkoxysilane compounds of Formula I and their use as functional fluids also have now been developed.

DETAILED DESCRIPTION OF THE PREFERRED EMBODIMENT

The compounds of Formula I are prepared according to the invention by reacting an alkoxysilanol cluster compound of the general formula:

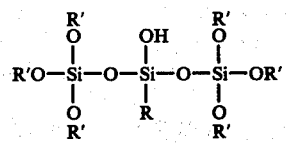

wherein R and R' are as defined in Formula I above, with a dihalo silicon bridging compound of the general formula:

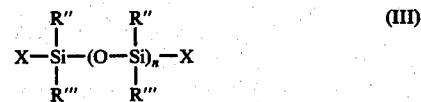

wherein X is any halogen and $n$, R'' and R''' are as defined above in Formula I.

The alkoxysilanol cluster compound reactant of Formula II is known in the art and is defined and can be prepared according to U.S. Pat. No. 3,965,135, issued to the present inventor. The cluster compound reactant wherein R is another —Si(OR')$_3$ group can be prepared in the manner as set forth in this cited patent except that a silicon tetrahalide is used in place of the trihalosilane in the reaction. The halogenated oxysilane cluster compound intermediate is shown in applicant's U.S. Pat. No. 3,992,429. These patents are hereby incorporated by reference in their entireties.

As defined above, the group R of the Formula II reactant is hydrogen, alkyl, alkenyl, aryl, aralkyl or —OSi(OR')$_3$. Preferably, R is hydrogen, alkyl or alkenyl having about 1 to about 18 carbon atoms or aryl or aralkyl having about 6 to about 24 carbon atoms. Most preferably, R is hydrogen, alkyl or alkenyl having about 1 to about 8 carbon atoms or aryl or aralkyl having about 6 to about 14 carbon atoms.

Also as defined above, R' groups of the Formula II reactant are independently selected from alkyl, alkenyl, aryl or aralkyl, with the proviso that at least a majority of the R' radicals are sterically hindered alkyl groups having at least 3 carbon atoms. Preferably, at least a majority of the R' radicals are sterically hindered alkyl groups having about 3 to about 24 carbon atoms and, most preferably, are all sterically hindered alkyl groups having about 4 to about 12 carbon atoms. By sterically hindered is meant alkyl radicals which contribute to the hydrolytic stability of the molecule, i.e., which inhibit the reaction of water with the silicon-oxygen or the carbon-oxygen bonds in the molecule. Exemplary of sterically hindered alkyl radicals are non-linear primary alkyl radicals having a beta position side chain of at least 2 carbon atoms, secondary alkyl radicals and tertiary alkyl radicals. Particularly useful sterically hindered groups include sec. butyl, isobutyl, 2-ethyl butyl, 2-ethyl pentyl, 3-ethyl pentyl, 2-ethyl hexyl, 3-ethyl hexyl, 2,4-dimethyl-3-pentyl, etc.

In the method for preparing these alkoxysilanol cluster reactants, a trihalosilane or a silicon tetrahalide is reacted with a trialkoxysilanol in the presence of a hydrogen halide acceptor base, and optionally, a solvent, to obtain an intermediate compound which is subsequently reacted with water to produce the cluster compound reactant of Formula II.

The dihalo silicon bridging reactant of Formula III also is known in the art. The groups R" and R"'can independently be selected from hydrogen, alkyl, aryl, aralkyl, hydroalkyl, and halo or cyano substituted alkyl, alkenyl, aryl, aralkyl and hydroalkyl. Lower alkyl and alkenyl groups of 1-4 carbons are preferred. The dihalo compounds can be simple silanes or polyalkyl, aryl, alkenyl or hydrido siloxanes of the general Formula III. The integer $n$ can be 0 or any positive value up to about 300. However, compounds featuring a relatively low value of $n$, e.g., $n = 0$ to 5, are preferred. Particularly preferred are dihalo compounds wherein $n = 0$ to 3. The halo constituents X may independently by any halogen, i.e., F, Cl, Br or I. Dichloro compounds are preferred.

These dihalo silanes and polysiloxanes may be prepared by known conventional procedures. For example, U.S. Pat. No. 2,380,999 and E. G. Rochow in J. Am. Chem. Soc. 67 963 (1945) disclose methods of preparing such organosilicon halides by reacting hydrocarbon halides with silicon. Typical synthesis of polysiloxanes by hydrolysis of organosilicon halides is shown by W. Patnode and D. F. Wilcock in J. Am. Chem. Soc. 68 358 (1946).

The alkoxysilanol cluster reactant (Formula II) and the dihalo silicon reactant (Formula III) are reacted in the presence of a hydrogen halide acceptor base compound. The acceptor base may be any compound which will accept hydrogen halide and thereby promote the formation of the double cluster compounds of the present invention pursuant to Equation A below. Among the preferred acceptors are the nitrogenated tertiary organic bases having at least 3 carbon atoms, e.g., the lower alkyl and aryl tertiary amines such as triethylamine, tributylamine, as well as pyridine is particularly preferred.

The reaction which occurs in formation of the novel double cluster compounds of the present invention using the above-described reactants may be represented by the following Equation A:

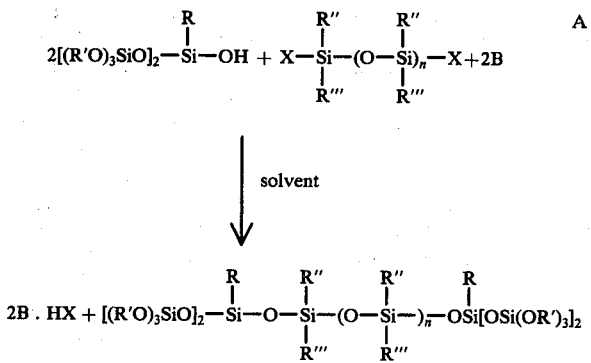

wherein B is a hydrogen halide acceptor base, and the other reactants are as described above in Formula II and III, respectively. The product, defined in Formula I above, is the double cluster alkoxysilanol compound of the present invention.

As indicated by the above Equation A, the reaction to formulate the subject double cluster alkoxysilanols preferably is carried out in a solvent medium. While use of a solvent is not required, it is preferred since it serves to moderate the rate of the reaction and enhances the separation of the base acceptor-hydrohalide (B.HX) from the double cluster compound product. The solvent medium may be any non-protonic solvent which does not interfere with the reaction outlined in Equation A. In addition, the reactants and the acceptor-base must be soluble in the chosen solvent, and the base acceptor-hydrohalide must be insoluble in the medium in order to facilitate its removal from the product compound. Preferred solvents include benzene, toluene, xylene, hexane, heptane, high-boiling petroleum ethers, and other ethers such as tetrahydrofurane, dioxane and the like.

In forming the double cluster alkoxysilanol compound according to Equation A above, any suitable proportions of reactants can be used. In general, about 1.7 to 5 moles of alkoxysilanol cluster reactant per mole of dihalo silicon bridging compound is used. Preferably, in order to enhance product formation and promote reaction completion, a stoichiometric amount of the reactants or a slight excess over the stoichiometric amount of alkoxysilanol cluster reactant is employed. Accordingly, it is preferred to use about a 2:1 to about a 3:1 molar ratio of cluster reactant to dihalo reactant.

The total amount of solvent, if used as a reaction medium, is not considered critical to the reaction. Favorable results can be achieved by using from about 0.5 to about 10 parts of solvent per part of total combined reactants by volume. Preferably, about 1 to 3 parts of solvent is used per part of total reactants by volume.

The hydrogen halide acceptor base can be used in any suitable proportion; it advantageously is used in about a stoichiometric amount, or in excess of the stoichiometric amount, based on Equation A. In general, about 2 to about 5 moles of acceptor base per mole of dihalo siloxane reactant is used. The preferred molar ratio is about 2.5:1 to about 3.5:1; utilizing such an excess of acceptor base is beneficial for completion of the reaction.

The reaction of Equation A may be conducted at a wide range of temperatures, from very low temperatures to room temperature to even very high temperatures, as long as no detrimental effect on reactants or product is initiated. Hence, the reaction temperature generally may range from about −40° to about 100° C or as high as the reflux temperature of the lowest boiling reactant or the solvent. To minimize side reactions and avoid loss of volatile dihalo siloxane reactant, it is preferred to carry out the reaction initially at low temperatures (about −10 to about 20° C) and then to finish the reaction at higher temperatures (about 50° to 100° C) to drive the reaction as far as possible to completion. Most preferably is a batch reaction scheme wherein a temperature range of about −5° to about +5° C is used for an initial period of about 0.5 to 2 hours during addition of reactants, followed by a finishing-up period of about 0.5 to about 12 hours at about 60° to about 90° C. A preferred batch reaction mixture is first to charge the reactor with the alkoxysilanol cluster reactant, the acceptor base, and a portion of solvent. Then, the reactor is cooled to within the specified temperature range, and, while stirring the mixture, a solution of the dihalo silane in an additional portion of solvent is added dropwise. Following completion of this addition, the reactor temperature is raised to within the specified range to complete the reaction. In practicing the reaction, a continuous operation may also be arranged whereby the first reactor in a series of reactors is maintained at the lower temperature and each subsequent reactor is incrementally higher in temperature to drive the reaction to completion.

The double cluster product can be separated from the resulting product mixture by conventional separation techniques such as filtrations and distillations. An advantageous routine is to remove the acceptor base-hydrohalide by filtration, followed by stripping of the solvent medium and fractionation. A preferred separation procedure, using a single reactor, is to water-wash the product mixture and phase-out the base-hydrohalide-containing aqueous layer. The product solution can then be dried with desiccants, or preferably dried by azeotroping the water with solvent, followed by solvent stripping and fractionation. The desired degree of purity of the final product, of course, determines the choice and extent of separation method.

The novel double cluster compounds of the present invention, as represented by Formula I above, contain a sufficient number of silicon atoms so as to exhibit favorable lubricating properties with no need for lubricity-improving additives. The sterically hindered alkyl constituents, described above, serve to shield the silicon atoms from attack by water. The novel double cluster compounds have good hydrolytic stability, good lubricating properties, and low ASTM viscosity indices. The double cluster compounds display these properties both in substantially pure form and in mixture with excess alkoxysilanol cluster reactant defined in Equation A. Accordingly, the invented compounds have been found to be particularly useful as functional fluids.

The functional fluid systems to which the present invention is directed includes hydraulic-type functional fluid systems and heat transfer-type functional fluid systems.

The hydraulic-type fluid systems include any system wherein a mechanical effort is converted to pressure at a first location, the pressure is transmitted from this first location to a second location via a hydraulic fluid, and the pressure is converted to a second mechanical effort at the second location. Thus, the hydraulic systems contemplated by the present invention include hydraulic brake systems, hydraulic steering mechanisms, hydraulic transmissions, hydraulic jacks and hydraulic lifts. Included among these are the hydraulic systems used in heavy equipment and transportation vehicles including highway and construction equipment, railways, planes and aquatic vehicles. Also included are special or custom fluid-requiring systems such as high pressure or temperature gradient systems including those employed in arctic environments as well as those found in aerospace and lunar vehicles and the like.

The heat transfer-type fluid systems include the hydraulic systems described above wherein heat is dissipated by the hydraulic fluid and include many other systems as well. In general, the present invention contemplates heat transfer systems wherein heat is passed from a first heat conductor at a first location to a heat transfer fluid, the heat is transmitted from the first location to a second location via the heat transfer fluid, and the heat is passed from the heat transfer fluid to a second conductor at the second location. Thus, the heat transfer systems of the present invention include heat dissipation systems, fluidic heating systems, e.g., radiator-type circulating fluid heating systems, heat exchange systems such as gas-liquid and liquid-liquid concurrent and countercurrent tubular heat exchangers as are used, for example, in the chemical process industries, cooling systems for nuclear reactors, radiator-type cooling systems, and any other temperature gradient systems in which a closed or sealed fluid heat transfer medium is used.

In the functional fluid systems of the present invention, the compounds of Formula I above are used in an effective amount. Due to the particularly advantageous hydrolytic stability of these compounds, as well as their high lubricity and low viscosity indices, the compounds may be used without any additives or diluents. Thus, by an effective amount of these compounds is meant the compound product without additional components as well as fluids containing additional fluid components. In one embodiment, the compounds of Formula I may be employed without additives or diluents. Alternatively, these compounds may comprise the base component of a functional fluid or may constitute a minor component, e.g., an additive, in a functional fluid containing a different base component. In general, an effective amount may be any amount which will produce the desired fluid characteristics for a given system. Therefore, as little as 5% or less of one or more of the compounds of Formula I may be used or as much as about 100% of the compounds may be used, percentages by weight. For example, 20 to about 95% or about 100% of the functional fluid may be one or more of the compounds of Formula I, e.g., 45 to 90% of the fluid may comprise one or more compounds of Formula I.

Various diluents, inhibitors and other additives are well known in the functional fluid art and these may optionally be added to the functional fluids used in the systems of the present invention, if desired. For example, a diluent component may be one or more glycol monoethers of diethers of the formula:

IV 

wherein $R_1$ is an alkyl of 1 to 4 carbon atoms; $R_2$ is alkylene of 2 to 4 carbon atoms; $R_3$ is hydrogen or an alkyl of 1 to 4 carbon atoms; and $x$ is an integer from 2 to 4. The $R_1$, $R_2$ and $R_3$ groups may be straight chained or branched and the alkylene oxide group $OR_3$ in the above formula may comprise mixtures of alkylene oxides. Also included among the possible diluents are one or more glycols, such as the alkylene glycols, having the formula:

V 

wherein $R_4$ is an alkylene of 2 to 3 carbon atoms and $y$ is an integer from 1 to 5.

Illustrative of the above-described diluents are the following: diethylene glycol monoethyl ether, diethylene glycol monobutyl ether, triethylene glycol monomethyl ether, triethylene glycol monoethyl ether, tetraethylene glycol monomethyl ether, ethylene glycol, propylene glycol, diethylene glycol and tetraethylene glycol. Various other diluents and mixtures thereof, which are well known in the art may also be used with the organosilane containing base component of this invention. U.S. Pat. No. 3,377,288 discloses various diluents which may be utilized.

Generally, the particular amount of diluents which is used is not critical and widely varying amounts may be used. More particularly, the diluent components may constitute from 0 up to about 80% by weight of the fluid and preferably from about 20 to about 60%.

Various additives may be added to the fluids used in the systems of this invention to control or modify various chemical and physical properties. Among the various types of additives which can be added to the fluids are included inhibitors for pH and corrosion control, antioxidants, rust inhibitors, viscosity index improvers, pour point depressants, lubricating additives, antifoamants, stabilizers, vapor phase corrosion inhibitors, rubber swelling adjusters, demulsifiers, dyes and odor suppressants. Generally, the total amount of additives which may be incorporated into the fluid composition will vary between about 0 to about 20%, e.g., from about 0.1 to 8% and more specifically from about 0.2 to about 5% by weight, based on the total weight of the fluid composition.

For example, alkaline inhibitors for pH and corrosion control may optionally by employed in an amount sufficient to maintain alkaline conditions in the fluid compositions, e.g., at an apparent pH value of from about 7 to about 11.5, if desired. These inhibitors may generally be added in an amount of from about 0 to about 8% by weight based on the total weight of fluid compositions, e.g., from about 0.5 to about 6%. Useful alkaline inhibitors include, for example, alkali metal salts of higher fatty acids such as potassium oleate, the potassium soap of rosin or tall oil fatty acids, amines such as morpholine and ethanolamine and amine salts such as mono- or dibutyl ammonium borates.

An antioxidant may optionally be used, if desired. Typical antioxidants include, 2,2-di-(4-hydroxyphenyl) propane, phenothiazine, amines such as phenylalphanaphthylamine and hindered phenols such as dibutyl cresol. Generally, the amount of antioxidant used will vary from 0 to about 3% by weight, e.g., from about 0.001 to about 2% by weight based on the total weight of the fluid composition.

Additionally, other additives, if desired, may be incorporated into the fluid composition. For example, corrosion inhibitors such as butynediol and rubber swelling adjusters such as dodecyl benzene may be used.

The above-noted inhibitors and additives are merely exemplary and are not intended as an exclusive listing of the many well-known materials which can be added to fluid compositions to obtain various desired properties. Other illustrations of additives and diluents which may be used can be found in U.S. Pat. No. 3,377,288 and in "Introduction to Hydraulic Fluids" by Roger E. Hatton, Reinhold Publishing Corp. (1962).

The following examples depict various embodiments of the present invention; they are intended to be illustrative and not limiting in nature. All parts and percentages are by weight unless otherwise specified.

EXAMPLE I

A one liter three-neck flask is equipped with a stirrer, a reflux condenser, a thermometer, and an equilibrated dropping funnel. To avoid introduction of moisture, the reflux condenser is fitted with a $CaCl_2$ tube. The flask is charged with 154.9 g (0.264 moles) of alkoxysilanol cluster compound having the formula $CH_3Si[OSi(OC_4H_9 sec.)_3]_2OH$, hereinafter referred to as ASC. This ASC reactant was prepared according to the process set forth in U.S. Pat. No. 3,965,135, Example I. 29.2 g. (0.37 moles) of pyridine (acceptor base) and 400 ml of heptane solvent medium also is added. The mixture is stirred, maintained at $-5°$ C, and while blanketing the mixture with dry $N_2$, introduced through the equilibrated funnel, a solution of 17.06 g (0.132 moles) of dimethyldichloro silane dissolved in 80 ml of n-heptane is gradually added drop-wise. The gradual addition is completed in about 1 hour, after which the reaction mixture is heated to and maintained at 70° C for about 12 hours. The reaction mixture then is allowed to cool; 200 ml of water is added to the cooled mixture to dissolve the acceptor base-hydrohalide. The aqueous pyridine-hydrochloride layer is phased off. To complete the washing and to hydrolize any small amounts of unreacted Si · Cl bonds, an additional water wash, of 30 minutes duration, is repeated twice. Following the third water wash routine, the water is analyzed to be Cl⁻ free. The organic product phase then is dried over $CaCl_2$ (15 g) for 2 hours. The solvent now is removed by stripping in vacuo, using a rotary evaporator. The remaining fluid is fractionated using a micro distillation apparatus with a Vigreux column in vacuo. After forecuts totalling 30.8 g, the desired compound is obtained, boiling at 255± 3° C/0.05 mm. The 96.4 g of product is calculated to be a 59.5% yield, based on the amount of ASC originally charged.

The product double cluster alkylsilanol compound of the present invention has the formula:

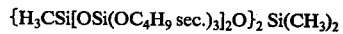

Based on the generic formula $C_{52}H_{120}O_{18}Si_7$, the calculated component amounts are C-50.77%; H-9.83%; Si-15.98%. The product was analyzed to contain C-50.21%, 50.41%; H-9.68%, 9.85%; Si-15.63%, 15.7%. A product of 1268 molecular weight was found, in good agreement with the theoretical molecular weight of 1230.

EXAMPLE II

The procedure of Example I is repeated, using, however, the following reactants, amounts, and conditions:

Flask Charge:

118.95 g (0.203 mole) ASC
22.48 g (0.284 mole) pyridine
300.00 ml n-heptane

The initial reaction, during addition of 20.62 g (0.1014 mole) of 1,1,-3,3-tetramethyl, 1-3 dichlorodisiloxane in 100 ml of n-heptane, was conducted at +5° C (about 1 hour addition time). This initial period was followed by heating to and maintaining at 70° C for about 12 hours. Fractionation gives 98.7 g (74.6% yield) of the double cluster product

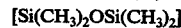

Based on the generic formula for the compound $Si_8C_{54}H_{126}O_{19}$, the theoretical calculated component amounts are C-49.73%, H-9.74%; Si-17.23%. The product was analyzed to contain C-49.98%, 50.06%; H-9.69%, 9.85%; Si-17.14%, 17,10%, Calculated product molecular weight was 1295 in comparison with the theoretical value of 1304.

EXAMPLE III

The procedure of Example I is repeated, using, however, the following reactants, amounts, and conditions:

Flask Charge:

108.45 (0.17 mole) ASC-assay 91.97%
20.0 g (0.253 mole) pyridine
200 ml n-heptane The initial reaction, during the addition of 25.66 g (0.092 mole 1,1-3,3-5,5-hexamethyl,1,5 dichlorotrisiloxane in 80 ml of n-heptane, was conducted at 0° C for 1 hour. The initial low temperature reaction period was followed by heating the flask to 70° C and maintaining it at that temperature for about 12 hours.

After the usual work-up and fractionation, 85.1 g of the desired product was recovered at 255± 3° C/10$^{-3}$ mm. Based on the flask charge of ASC, this represents a 66.7% yield.

The double cluster product

[Si(CH$_3$)$_2$OSi(CH$_3$)$_2$OSi(CH$_3$)$_2$]

has the generic formula Si$_9$C$_{56}$H$_{132}$O$_{20}$. The theoretical component proportions are C-48.8%, H-9.65%; Si-18.34%. The product was analyzed to contain C-48.66%, 48.71%; H-9.43%, 9.51%, Si-18.15%. Calculated product MW was 1402, in good agreement with the theoretical MW 1378.

EXAMPLE IV

The general procedure of Example I is followed using the following reactants, amounts, and conditions:

Flask Charge:

120.3 g (0.186 mole) ASC-assay 90.63%
22.8 g (0.288 mole) pyridine
200 ml n-heptane During the addition of 17.78 g (0.093 mole) methylphenyl-dichlorosilane, the reactor was maintained at −5° C for about one hour. After addition was complete, the reactor was heated to 70° C and held there for about 12 hours.

The product mixture then was worked-up and fractionated in the usual manner. 73.2 g of the desired product was isolated, boiling at 265° C/0.02 mm. This represents a 60.9% yield, based on ASC charged.

The double cluster product

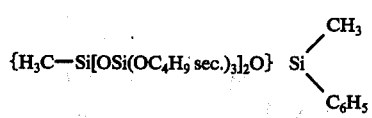

with the generic formula Si$_7$C$_{57}$H$_{122}$O$_{18}$, has the theoretical component proportions: C-52.98%; H-9.52%; Si-15.21%. The product was analyzed to contain C-52.65%, 52.81%; H-9.55%, 9.53%; Si-15.29%.

Calculated product MW 1247 is in good agreement with the theoretical MW 1292.

EXAMPLE V

The general procedure of Example I is followed with the following reactants, amounts, and conditions:

Flask Charge 164.37 g (0.28 mole) ASC
35.0 g (0.442 mole) pyridine
220 ml n-heptane During addition of 19.75 g (0.14 mole) methylvinyl-dichloro-silane in 100 ml n-heptane, the reactor was maintained at −5° C, for about one hour. Upon completion of the addition, the reactor was heated to 85° C and held there for about 12 hours.

The product mixture was worked up and fractionated in the usual manner. The desired product, 117.1 g, was obtained at 256± 2° C/10$^{-3}$ mm. This represents a 67.3% yield of the product

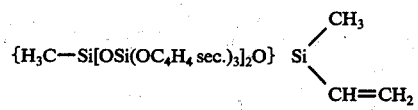

This compound has the generic formula Si$_7$C$_{53}$H$_{120}$O$_{18}$ which is caculated to contain the component proportions; C-51.25%, H-9.74%, Si-15.83%. Analysis of the actual product was C-51.30%, 51.13%; H-9.36%, 9.42%; Si-15.94%, 15.97%. Calculated product MW 1269 is in good agreement with the theoretical MW 1242.

EXAMPLE VI

The general procedure of Example I is followed, using the following reactants, amounts, and conditions:

Flask Charge:

96.52 g (0.164 mole) ASC
19.51 g (0.246 mole) pyridine
120 ml n-heptane

The reactor was maintained at 0° C for one hour during the addition of 9.46 g (0.082 mole) of methyldichlorosilane in 100 ml of n-heptane. The reaction mixture was then heated to 90° C and maintained at that temperature for about 12 hours.

The product mixture was worked-up and fractionated in the usual manner to yeild 69.0 g, at 255° C/0.02 mm., of the product

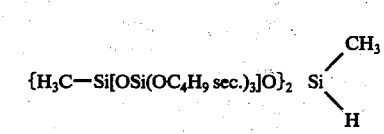

Based on the amount of ASC charged, a product yield of 69.05% was obtained.

The product double cluster compound has the generic formula Si$_7$C$_{51}$H$_{118}$O$_{18}$, which is calculated to contain C-50.37%; H-9.78%; Si-16.17%. The actual product was analyzed to contain C-50.16; H-9.71; Si-16.13.

Product MW was 1195, in good agreement with the theoretical MW 1216.

The above-described products obtained from each of the foregoing examples were tested for viscosity, flash point, weight loss, wear scar, and hydrolysis solids, as reported in Table I below. The viscosity index (ASTM D 22 70) is an expression of the effect of temperature on the viscosity of the product. The wear scar test is performed with a four ball 40 kg load apparatus at 1800 rpm and 168° F for one hour. The hydrolytic stability test is carried out at 210° F in the presence of one-third weight H$_2$O and copper metal catalyst for 100 hours. The results establish the favorable functional fluid properties of the invented double cluster compounds.

TABLE 1

Properties of Double Clusters $[(R'O)_3SiO]_2\text{—}\overset{R}{\underset{|}{S}}\text{—}O\text{—}\overset{R''}{\underset{R'''}{\overset{|}{Si}}}\text{—}(O\text{—}\overset{R''}{\underset{R'''}{\overset{|}{Si}}}\text{—})_n\text{-}O\text{—}\overset{R}{\underset{|}{S}}\text{—}[OSi(OR')_3]_2$

| COMPOUND | VISCOSITY CS −40° F | VISCOSITY CS 100° F | VISCOSITY CS 210° F | VISCOSITY INDEX | FLASH POINT SETA °F | WEIGHT LOSS% at 400° F/ 1 HR. | SCAR 4-Ball mm | HYDROLYTIC STABILITY % SOLIDS |
|---|---|---|---|---|---|---|---|---|
| PRODUCT OF EXAMPLE I | 1321 | 45.52 | 12.98 | 312 | 430 | 2.60 | 0.58 | 0.017 |
| PRODUCT OF EXAMPLE II | 922 | 38.30 | 11.51 | 322 | 435 | 3.24 | 1.05 | 0.026 |
| PRODUCT OF EXAMPLE III | 777 | 37.78 | 11.69 | 337 | 465 | 2.92 | 1.51 | 0.082 |
| PRODUCT OF EXAMPLE IV | 3075 | 71.73 | 18.09 | 285 | 430 | 1.40 | 0.64 | 0.025 |
| PRODUCT OF EXAMPLE V | 1608 | 53.67 | 14.90 | 306 | 425 | 2.83 | 0.38 | 0.031 |
| PRODUCT OF EXAMPLE VI | 745.5 | 35.13 | 10.76 | 328 | 440 | 1.56 | 0.70 | 0.019 |

I claim:

1. A compound having the formula:

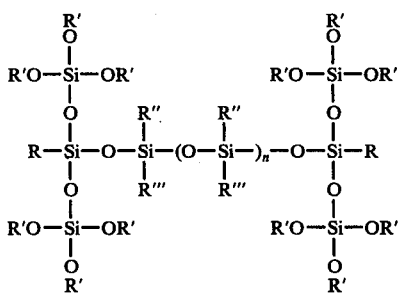

wherein $n$ is an integer from 0 to 300; R is hydrogen, alkyl, alkenyl, aryl, aralkyl or —OSi(OR')$_3$; each R' is independently selected from alkyl, alkenyl, aryl or aralkyl with the proviso that at least a majority of R' radicals are sterically hindered alkyl groups having at least 3 carbon atoms; and R" and '" are independently selected from hydrogen, alkyl, alkenyl, aryl, aralkyl, hydroalkyl, and halo or cyano substituted alkyl, alkenyl, aryl, aralkyl, and hydroalkyl.

2. The compound of claim 1 wherein at least a majority of the R' groups are sterically hindered alkyl groups having about 3 to about 24 carbon atoms.

3. The compound of claim 2 wherein the R' groups are sterically hindered alkyl groups having about 4 to about 12 carbon atoms.

4. The compound of claim 1 wherein $n$ is an integer from 0 to 5.

5. The compound of claim 4 wherein $n$ is an integer from 0 to 3.

6. The compound of claim 1 wherein R is hydrogen, alkyl or alkenyl having about 1 to about 18 carbon atoms or aryl or aralkyl having about 6 to about 24 carbon atoms, and each R' is independently selected from alkyl or alkenyl having about 1 to about 24 carbon atoms or aryl or aralkyl having about 6 to about 24 carbon atoms, subject to the proviso that at least a majority of the R' groups are sterically hindered alkyl groups having about 3 to about 24 carbon atoms.

7. The compound of claim 6 wherein R is hydrogen, alkyl or alkenyl having about 1 to about 8 carbon atoms or aryl or aralkyl having about 6 to about 14 carbon atoms, and each R' is independently selected from alkyl or alkenyl having about 1 to about 12 carbon atoms or aryl or aralkyl having about 6 to about 14 carbon atoms, subject to the proviso that at least a majority of the R' groups are sterically hindered alkyl groups having about 4 to about 12 carbon atoms.

8. The compound of claim 1 wherein R" and R'" are independently selected from lower alkyl and alkenyl of about 1 to about 4 carbon atoms.

9. The compound of claim 7 wherein R" and R'" are independently selected from lower alkyl and alkenyl of about 1 to about 4 carbon atoms, and $n$ is an integer from 0 to 5, and the R' groups are all sterically hindered alkyl groups of about 4 to about 12 carbon atoms.

10. The compound of claim 1 wherein R is methyl, R' is sec-butyl, R" and R'" are selected from hydrogen, methyl, ethenyl and phenyl, and $n$ is an integer from 0 to 3.

11. A method of preparing the compound of claim 1 comprising:
reacting a dihalo silicon bridging compound of the formula:

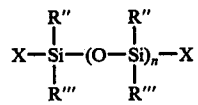

wherein X is any halogen and $n$, R" and R'" are as defined above in claim 1,
with an alkoxysilanol cluster compound, said alkoxysilanol cluster compound having the formula:

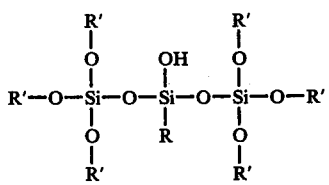

wherein R and R' are as defined above in claim 1, in the presence of a hydrogen halide acceptor base compound,
said reaction being conducted at a temperature ranging from about −30° C to about the relfux temperature of the lowest boiling reaction mixture ingredient.

12. The method of claim 11 wherein the alkoxysilanol cluster compound reactant is used in an amount ranging from about 1.8 to about 5 moles per mole of the dihalo silicon bridging compound.

13. The method of claim 12 wherein the halogen halide acceptor base compound is present in an amount ranging from about 2 to about 5 moles per mole of the dihalo silicon bridging compound.

14. The method of claim 13 wherein said reaction is conducted at an initial temperature range of about −10 to about 30 20° C for 0.5 to about 2 hours, during addition of reactants, followed by a reaction period of about 0.5 to about 12 hours at a temperature range of about 50 to about 100° C.

15. The method of claim 14 wherein said reaction is conducted in a solvent medium comprising about 0.5 to about 10 parts of solvent per part of total reactants by volume.

16. The method of claim 15 wherein X is Cl, $n$ is an integer from 0 to 5, R is hydrogen, alkyl or alkenyl having about 1 to about 18 carbon atoms or aryl or aralkyl having about 6 to 24 carbon atoms and each R' is indepedently selected from alkyl or alkenyl of about 1 to about 24 carbon atoms or aryl or aralkyl of about 6 to about 24 carbon atoms subject to the proviso that at least a majority of the R' groups are sterically hindered alkyl groups having from 3 to about 24 carbon atoms.

17. The method of claim 16 wherein $n$ is an integer from 0 to 3, R is hydrogen, alkyl or alkenyl having about 1 to about 8 carbon atoms or aryl or aralkyl having about 6 to about 14 carbon atoms, and each R' is independently selected from alkyl or alkenyl having about 1 to about 12 carbon atoms or aryl or aralkyl having about 6 to about 14 carbon atoms subject to the proviso that at least a majority of the R' groups are sterically hindered alkyl groups having from about 4 to about 12 carbon atoms.

18. The method of claim 17 wherein X is Cl, R is methyl, R' is sec-butyl, R" and R'" are selected from hydrogen, methyl, ethenyl and phenyl, and $n$ is an integer from 0 to 3.

* * * * *

UNITED STATES PATENT OFFICE
CERTIFICATE OF CORRECTION

Patent No. 4,058,546      Dated November 15, 1977

Inventor(s) Karl O. Knollmueller

It is certified that error appears in the above-identified patent and that said Letters Patent are hereby corrected as shown below:

Column 1, line 30, "silicon-bridged" should read --silicone-bridged--.

Column 2, line 29, after "another", "-Si(OR')$_3$" should read -- -OSi(OR')$_3$--.

Column 3, line 38, after "pyridine", insert --, substituted pyridine, N,N'-dimethylaniline, etc. Pyridine--.

Column 3, line 60, "Formula" should read --Formulas--.

Column 4, line 16, "1.7" should read --1.8--.

Column 4, line 28, after "about 1 to", insert --about--.

Column 4, line 52, "preferably" should read --preferable--.

Column 4, line 57, after "reaction", "mixture" should read --routine--.

Column 6, line 35, "IV" should be brought back out to the margin.

Column 6, line 46, "V" should be brought back out to the margin.

UNITED STATES PATENT OFFICE
CERTIFICATE OF CORRECTION

Patent No. 4,058,546           Dated November 15, 1977

Inventor(s) Karl O. Knollmueller

It is certified that error appears in the above-identified patent and that said Letters Patent are hereby corrected as shown below:

Column 7, line 13, after "optionally", "by" should read --be--.

Column 7, line 28, "alphanaphthylamine" should read --alpha-naphthylamine--.

Column 8, line 9, "Cl-free" should read --Cl⁻ free--.

Column 8, line 50, after "C-49.73%", the comma (,) should be a semicolon (;).

Column 8, line 52, after "Si-17.14%,", "17,10%" should read --17.10%--.

Column 8, line 65, "(0.092 mole" should read --(0.092 mole)--.

Column 9, line 13, after "C-48.8%", the comma (,) should be a semicolon (;).

Column 9, line 15, after "9.51%", the comma (,) should be a semicolon (;).

UNITED STATES PATENT OFFICE
CERTIFICATE OF CORRECTION

Patent No. 4,058,546   Dated November 15, 1977

Inventor(s) Karl O. Knollmueller

It is certified that error appears in the above-identified patent and that said Letters Patent are hereby corrected as shown below:

Column 10, line 10, the formula " 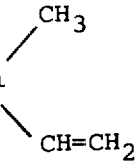 "

should read -- 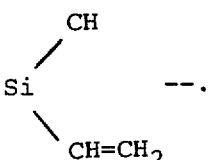 --.

Columns 11 and 12, in Table I, in the line of "PRODUCT OF EXAMPLE VI" under the heading "Viscosity Cs/-40°F", "745.5" should read --746.5--.

Column 11, line 39, in claim 1, " ''' " should read --R'''--.

Column 12, line 62, in claim 11, "relfux" should read --reflux--.

Column 13, line 7, in claim 14, "30 20°C" should read --+20°C--.

Signed and Sealed this

Sixteenth Day of May 1978

[SEAL]

Attest:

RUTH C. MASON
Attesting Officer

LUTRELLE F. PARKER
Acting Commissioner of Patents and Trademarks

UNITED STATES PATENT OFFICE
CERTIFICATE OF CORRECTION

Patent No. 4,058,546    Dated November 15, 1977

Inventor(s) Karl O. Knollmueller

It is certified that error appears in the above-identified patent and that said Letters Patent are hereby corrected as shown below:

Column 1, line 30, "silicon-bridged" should read --silicone-bridged--.

Column 2, line 29, after "another", "-Si(OR')$_3$" should read -- -OSi(OR')$_3$--.

Column 3, line 38, after "pyridine", insert --, substituted pyridine, N,N'-dimethylaniline, etc. Pyridine--.

Column 3, line 60, "Formula" should read --Formulas--.

Column 4, line 16, "1.7" should read --1.8--.

Column 4, line 28, after "about 1 to", insert --about--.

Column 4, line 52, "preferably" should read --preferable--.

Column 4, line 57, after "reaction", "mixture" should read --routine--.

Column 6, line 35, "IV" should be brought back out to the margin.

Column 6, line 46, "V" should be brought back out to the margin.

UNITED STATES PATENT OFFICE
CERTIFICATE OF CORRECTION

Patent No. 4,058,546                    Dated November 15, 1977

Inventor(s) Karl O. Knollmueller

It is certified that error appears in the above-identified patent and that said Letters Patent are hereby corrected as shown below:

Column 7, line 13, after "optionally", "by" should read --be--.

Column 7, line 28, "alphanaphthylamine" should read --alpha-naphthylamine--.

Column 8, line 9, "Cl-free" should read --$Cl^-$ free--.

Column 8, line 50, after "C-49.73%", the comma (,) should be a semicolon (;).

Column 8, line 52, after "Si-17.14%,", "17,10%" should read --17.10%--.

Column 8, line 65, "(0.092 mole" should read --(0.092 mole)--.

Column 9, line 13, after "C-48.8%", the comma (,) should be a semicolon (;).

Column 9, line 15, after "9.51%", the comma (,) should be a semicolon (;).

UNITED STATES PATENT OFFICE
CERTIFICATE OF CORRECTION

Patent No. 4,058,546  Dated November 15, 1977

Inventor(s) Karl O. Knollmueller

It is certified that error appears in the above-identified patent and that said Letters Patent are hereby corrected as shown below:

Column 10, line 10, the formula " $\{H_3C-Si[OSi(OC_4H_4sec.)_3]_2O\} Si\begin{smallmatrix}CH_3\\ \\CH=CH_2\end{smallmatrix}$ "

should read -- $\{H_3C-Si[OSi(OC_4H_9sec.)_3]_2O\} Si\begin{smallmatrix}CH_3\\ \\CH=CH_2\end{smallmatrix}$ --.

Columns 11 and 12, in Table I, in the line of "PRODUCT OF EXAMPLE VI" under the heading "Viscosity Cs/-40°F", "745.5" should read --746.5--.

Column 11, line 39, in claim 1, " ''' " should read --R'''--.

Column 12, line 62, in claim 11, "relfux" should read --reflux--.

Column 13, line 7, in claim 14, "30 20°C" should read --+20°C--.

This certificate supersedes Certificate of Correction issued May 16, 1978.

Signed and Sealed this

Twenty-sixth Day of September 1978

[SEAL]

Attest:

RUTH C. MASON
Attesting Officer

DONALD W. BANNER
Commissioner of Patents and Trademarks